United States Patent
Szeles (10) Patent No.: US 8,942,814 B2
(45) Date of Patent: Jan. 27, 2015

(54) PUNCTUAL STIMULATION DEVICE

(75) Inventor: Josef Constantin Szeles, Vienna (AT)

(73) Assignee: Dr. Jozsef Constantin Szeles, Vienna (AT)

(*) Notice: Subject to any disclaimer, the term of this patent is extended or adjusted under 35 U.S.C. 154(b) by 166 days.

(21) Appl. No.: 13/395,988

(22) PCT Filed: Sep. 13, 2010

(86) PCT No.: PCT/IB2010/002261
§ 371 (c)(1),
(2), (4) Date: May 25, 2012

(87) PCT Pub. No.: WO2011/030210
PCT Pub. Date: Mar. 17, 2011

(65) Prior Publication Data
US 2012/0226333 A1    Sep. 6, 2012

(30) Foreign Application Priority Data
Sep. 14, 2009 (AT) .................. 572/2009 U (51) Int. Cl.
A61N 1/00 (2006.01)
A61H 39/00 (2006.01)
A61N 1/36 (2006.01)

(52) U.S. Cl.
CPC .......... *A61H 39/002* (2013.01); *A61N 1/36014* (2013.01); *A61N 1/36032* (2013.01);
(Continued)

(58) Field of Classification Search
USPC .................... 607/45–46, 59, 57, 72
See application file for complete search history.

(56) References Cited

U.S. PATENT DOCUMENTS

2006/0195158 A1*  8/2006  Cory ............................. 607/46
2010/0161008 A1*  6/2010  Hase et al. ................... 607/72
(Continued)

FOREIGN PATENT DOCUMENTS

WO     86/02567 A1     5/1986
WO     2004/000413 A2  12/2003
WO     2008/128270 A2  10/2008

OTHER PUBLICATIONS

Sator-Katzenschlager S M et al: "The Short- and Long-Term Benefit in Chronic Low Back Pain Through Adjuvant Electrical Versus Manual Auricular Acupuncture" in: Anesthesia and Analgesia, Williams and Wilkins, Baltimore, MD, US, vol. 98, Jan. 1, 2004, pp. 1359-1364.

(Continued)

*Primary Examiner* — Catherine Voorhees
(74) *Attorney, Agent, or Firm* — Joyce von Natzmer; Agris & von Natzmer LLP (57) ABSTRACT

Disclosed is a device for the punctual stimulation of the nerve endings located in the region of the ears The device has a battery-powered therapeutic current generator (3) arranged in a housing (4) which is to be worn in the region of the ear. The generator supplies a low frequency therapeutic current and has a plurality of output channels (9a, 9b, 9c). Each output channel is associated with its own stimulation electrode (6a, 6b, 6c), and contains an amplifier (15a, 15b, 15c), controlled by a digital-analog converter (12) and designed for bipolar output signals. A control signal may be fed to the amplifiers causing current strength and stimulation voltage behavior in the output circuit of the respective amplifier. The behavior adapts to the resistance value in said circuit and corresponds to $I=k\cdot R$ $U=k\cdot R^2$, in which k is a selectable constant. In addition, three output channels are preferably provided, each associated with its own stimulation electrode, and during the periods of current flow, the therapeutic current fed to each stimulation electrode is compensated each time with regard to the intensity and polarity by the therapeutic currents being fed to the other stimulation electrodes.

24 Claims, 5 Drawing Sheets

(52) U.S. Cl.
CPC . *A61H2201/5035* (2013.01); *A61H 2201/5058* (2013.01); *A61H 2205/027* (2013.01); *A61N 1/36017* (2013.01); *A61N 1/36021* (2013.01); *A61N 1/36053* (2013.01)
USPC .............................................. 607/46; 607/45

(56) References Cited

U.S. PATENT DOCUMENTS

2010/0168822 A1    7/2010  Szeles
2010/0213857 A1*   8/2010  Fan ............................... 315/186
2013/0131755 A1*   5/2013  Panken et al. ................... 607/45

OTHER PUBLICATIONS

Kaniusas E et al: "Adaptive auricular electrical stimulation controlled by vital biosignals. Transition from fixed to adaptive and synchronized electrical stimulation controlled by heart rate variability and blood perfusion" in: Proceedings of the Second International Conference on Biomedical Electronics and Devices, Biodevices 2009; Porto, Portugal, January 14-17, 2009, INSTICC PR, PT, Jan. 14, 2009, pp. 304-309.

* cited by examiner

FIG. 1

LEGEND

| | | |
|---|---|---|
| 1. Device for punctual stimulation | 11. Internal storage | 21. Constant current control circuit |
| 2. Ear | 12. Digital-analog converter | 22. Adaptive current control circuit |
| 3. Therapeutic current generator | 13. Digital Connection | 23. Constant-voltage feedback control circuit |
| 4. Housing | 14. (a, b, c) Outputs | 24. Constant-current feedback control circuit |
| 5. (a, b, c) Flexible lines | 15. (a, b, c) Amplifiers | 25. Adaptive current feedback control circuit |
| 6. (a, b, c) Output channel stimulation electrode | 16. (a, b, c) Current paths | 26. Resistance calculating circuit |
| 7. Needle electrode | 17. (a, b, c) Measuring resistors | 27. Supply battery |
| 8. Flexible connection | 18. (a, b, c) Measuring amplifiers | 28. Antenna |
| 9. (a, b, c) Analog output channels | 19. (a, b, c) Measuring circuits | 29. Operating transmission device |
| 10. Microcomputer circuit | 20. Constant voltage control circuit | |

LEGEND
40. Voltage Transformer
41. Supply Connection
42. Switching Device
43. Voltage Transformer
44. Schottky diode under the US 8,942,814 B2

PUNCTUAL STIMULATION DEVICE

CROSS-REFERENCE TO RELATED APPLICATIONS

This is the U.S. national stage of International application PCT/IB2010/002261, filed Sep. 13, 2010 designating the United States and claiming priority to Austrian application no. GM 572/2009, filed Sep. 14, 2009.

BACKGROUND OF THE INVENTION

The invention relates to a device for the punctual stimulation of endings of nerves which are located in the region of the ears and run to the brainstem nuclei, said device having a battery-powered therapeutic current generator which is arranged in a housing to be worn in the region of the ear and is provided with an electronic circuit forming a low-frequency therapeutic current, and which device further has at least two flexible lines extending from the therapeutic current generator for connecting in each case to a stimulation needle electrode to be positioned at a nerve ending.

SUMMARY OF THE INVENTION

It is an object of the invention to provide a device of the aforementioned type which offers a larger spectrum of possibilities with regard to the details of stimulation and therefore allows to achieve a broader range of therapeutic application. Also, it shall be possible for the device to be provided that the effect of influences which can affect the stimulation, e.g., the effect of forces acting from the outside on the electrodes, or the effect of changes of the resistance values in the electrode region, can be kept small or can be compensated.

The device according to the invention of the aforementioned type is characterized in that the therapeutic current generator has a plurality of analog output channels, wherein each of these output channels is associated with its own stimulation electrode, and these analog output channels for controlling the therapeutic current are each individually connected to a micro-computer circuit in which the parameter values for the therapeutic currents provided for the respective therapy can be stored in a storage to be available for a continuous readout. With this configuration, the above-mentioned object can be readily achieved. For example, in the case of an externally caused loosening of the fit of a stimulation electrode with an initially good electrical conductivity or, e.g., in the case of a rapid increase of the electrical resistance of the subcutaneous tissue at the injection site of a stimulation electrode, the stimulating function of the respective stimulation electrode can be affected, but a stimulation, although a limited one, can still take place with another stimulation electrode which, as mentioned, is connected to its own output channel. Also, in the case of functional errors in the region of a reference electrode, the stimulation can be maintained by suitably controlling the output channels, which are independent of each other, in that a current flow is established which is fed through two or more stimulation electrodes. The presence of a plurality of output channels offers also the possibility to stimulate, at different receptor regions at which different nerve endings are located, with therapeutic currents which differ in terms of their parameters. Thus, at different places of the ear, stimulation with different intensity can be provided and, e.g., parasympathetic and sympathetic nerve cords can optionally be stimulated. The parameters of the therapeutic currents can be selected or set in a simple manner in wide ranges, wherein, e.g., a change can take place from therapeutic currents of high intensity, which are formed from a series of pulse packets and are in particular suitable for pain therapy in the acute stage, to therapeutic currents of low intensity which are formed by individual pulses and are in particular suitable for pain therapy in the case of chronic pain, wherein it is also possible during such a treatment to provide a slow increase of the intensity at the beginning of the treatment and a slow decay at the end of it.

A preferred embodiment of the device according to the invention is characterized in that in the individual output channels in each case one amplifier is provided which is controlled by a digital-analog converter and configured for bipolar output signals, wherein the digital-analog converter, for its part, is connected to a digital connection of the micro-computer circuit. Hereby, a favorable implementation can be obtained if in the individual output channels, operational amplifiers are provided as amplifiers.

Gathering the in each case occurring values of the currents fed during a stimulation treatment to the stimulation electrodes and the voltages in each case present at these stimulation electrodes is of advantage for programming the parameters of the therapeutic currents and for maintaining the same during the stimulation. For this, it is provided according to preferred embodiments of the device according to the invention, on the one hand, that in the output channels, in the current paths running to the stimulation electrodes, measuring resistors for current measurement are inserted and that to the individual measuring resistors in each case one measuring amplifier is connected, the output signal of which is a measure for the current strength of the therapeutic current and is fed to the micro-computer circuit, and, on the other hand, it is provided that at least at one output channel, a voltage measuring circuit is provided which outputs to the micro-computer circuit a measurement signal which corresponds to the voltage which is present between the stimulation electrode associated with the relevant output channel and a reference potential point which is located in the therapeutic current generator and is preferably connected to a reference electrode.

A design of the device according to the invention which is in particular advantageous with regard to a selectable setting of the intensity of the therapeutic currents and which also offers the advantage that in the case of an unintentionally occurring increase of the electrical resistance in the circuits fed through the stimulation electrodes, which increase can be a result of resistance increases in the skin or in the subcutaneous tissue or of a loosening of the fit of a stimulation electrode, no voltage peaks are created which, under certain circumstances, are perceived as unpleasant, is characterized in that in the micro-computer circuit, a constant-voltage control circuit is provided which is optionally activatable by external actuation and is operatively connected to an internal storage for therapy current parameters and which feeds a control signal via a digital-analog converter to at least one amplifier provided in an output channel, said control signal causing in the amplifier's output circuit connected to a stimulation electrode the behavior of a constant-voltage source which is adjustable with regard to the voltage value. It is further of advantage here if it is provided that in the constant-voltage control circuit, a constant-voltage feedback control circuit is integrated to which the measurement signal of the relevant voltage measurement circuit is fed as an actual signal.

If the focus is on maintaining a certain selected intensity of the therapeutic current, an embodiment of the device according to the invention is advantageous which is characterized in that in the micro-computer circuit, a constant-current control circuit is provided which is optionally activatable by external actuation and is operatively connected to an internal storage for therapeutic current parameters and which feeds a control signal via a digital-analog converter to at least one amplifier provided in an output channel, said control signal causing in the amplifier's output circuit connected to a stimulation electrode the behavior of a constant-voltage source which is adjustable with regard to the voltage value, and that in the constant-voltage control circuit, a constant-voltage feedback control circuit is integrated to which the measurement signal of the relevant voltage measurement circuit is fed as an actual signal.

Another configuration of the device according to the invention with which the advantageous property can be achieved that the sensation and the effect of the stimulation remains substantially unchanged even during the occurrence of changes of the electrical resistance in the respective stimulation circuit, wherein this applies to the treatment of many different medical conditions, is characterized in that in the micro-computer circuit, an adaptive-current control circuit is provided which is optionally activatable by external actuation and which is operatively connected to an internal storage for therapeutic current parameters and which feeds a control signal via a digital-analog converter to at least one amplifier provided in an output channel, said control signal causing in the amplifier's output circuit connected to a stimulation electrode a current strength and stimulation voltage behavior which adapts to the resistance value in said output circuit and corresponds to the relations $$I = k \cdot R \text{ and } U = k \cdot R^2$$

in which k is a selectable constant. It is advantageously provided here that in the adaptive-current control circuit, an adaptive-current feedback control circuit is integrated to which as an actual signal, a resistance measurement value is fed which is obtained from the measurement signal of the voltage measuring circuit and the output signal of the measuring amplifier of the current measurement. In particular, to achieve that a sensation accompanying the stimulation remains unchanged, a configuration of the device according to the invention is advantageous which is characterized in that the control circuit—which is provided in the micro-computer circuit and which feeds a control signal to the amplifiers provided in the output channels, which said signal, in a cyclical succession, forms time intervals in which a current flow to the stimulation electrodes takes place and time intervals in which the output channels are inactive, wherein in each case one current flow time interval and one inactive time interval together form one stimulation cycle—causes a variation of the current strength's average determined over the duration of a stimulation cycle by varying said duration through the control signal.

For a stimulation therapy in the case of certain disorders or illnesses and, e.g., for achieving a homogenous sensation at the entire ear it is advantageous to continuously change the polarity of the therapeutic currents. For this, a configuration of the inventive device is provided which is characterized in that during a current flow of the therapeutic currents fed to the individual stimulation electrodes, these stimulation electrodes, at the time considered in each case, have polarities which differ from each other with regard to a reference potential point which is connected with the therapeutic current circuits. This configuration results also in an at least partial relief of a reference electrode connected to the reference potential point from the therapeutic currents flowing through the stimulation electrodes. This effect applies to an even greater extent to a refinement which is characterized in that the therapeutic currents, which are fed to the individual stimulation electrodes which have polarities which differ from each other at the respectively considered time, compensate each other at the respectively considered time so that no therapeutic current flows through a reference electrode. In this manner, a reference electrode can be eliminated. It is further beneficial if it is provided that the control circuit—which is provided in the micro-computer circuit and which feeds a control signal to the amplifiers provided in the output channels, which said control signal, in a cyclical succession, forms time intervals in which a current flow to the stimulation electrodes takes place and time intervals in which the output channels are inactive, wherein in each case one current flow time interval and one inactive time interval together form one stimulation cycle, and wherein in the current flow time intervals, a therapeutic current flows in the form of a packet of successive pulses or in the form of a single pulse—causes a polarity reversal at each current flow time interval. It is preferably provided in this connection that the polarity reversal is caused within the current flow time intervals. This is often considered as being therapeutically beneficial.

From a therapeutic point of view and also with regard to a reduction or even avoidance of a therapeutic current flow through a reference electrode, a configuration of the inventive device is advantageous which is characterized in that the control circuit—which is provided in the micro-computer circuit and which feeds a control signal to the amplifiers provided in the output channels, which said signal, in a cyclical succession, forms time intervals in which a current flow to the stimulation electrodes takes place and time intervals in which the output channels are inactive, wherein in each case one current flow time interval and one inactive time interval together form one stimulation cycle—causes during the individual current flow time intervals one or a plurality of changes of the intensity of the therapeutic currents fed to the individual stimulation electrodes, wherein the intensity changes taking place at a respectively considered stimulation electrode run counter to the intensity changes taking place at one or a plurality of other respectively considered stimulation electrodes. This can be implemented even with only two output channels and stimulation electrodes; however, it seems to be more feasible with three or more output channels and stimulation electrodes. A preferred configuration is characterized in this context in that three output channels are provided, each of them associated with its own stimulation electrode, and the therapeutic current, which is fed within the current flow time intervals to each individual stimulation electrode is compensated with regard to intensity and polarity at each respectively considered point in time by the therapeutic currents which are fed in each case to the two other stimulation electrodes.

In particular focused on a pain therapy in chronic cases, but also suitable in other cases is a configuration of the device which is characterized in that the therapeutic currents fed to the individual stimulation electrodes are formed within each current flow interval by a single pulse and with each of these single pulses, a plurality of intensity changes and at least one polarity reversal are provided in chronological succession. Here, an implementation in connection with three output channels is preferred. For achieving the mentioned mutual compensation it is beneficial to provide that the one-time or repeated change of the therapeutic current intensity provided in the individual current flow intervals takes place incrementally.

As already mentioned above, it is advantageous for certain stimulation therapies, e.g. pain therapies for chronic disorders, to start with low values at the beginning of the treatment and to slowly increase the intensity of the stimulation to the full intended extent. For this, an embodiment of the device according to the invention is provided which is characterized in that the control circuit—which is provided in the micro-computer circuit and which feeds a control signal to the amplifiers provided in the output channels, which said signal, in a cyclical succession, forms time intervals in which a current flow to the stimulation electrodes takes place and time intervals in which the output channels are inactive, wherein in each case one current flow time interval and one inactive time interval together form one stimulation cycle—at the beginning of a stimulation cycle sequence formed by a multiplicity of successive stimulation cycles, continuously increases during a plurality of successive stimulation cycles from in each case one stimulation cycle to the next following stimulation cycle the intensity of the therapeutic current fed to a respectively considered stimulation electrode, the intensity being considered as average over the respective current flow time interval, and subsequently maintains during a multiplicity of successive stimulation cycles within their current flow time intervals the previously achieved level of intensity of the therapeutic currents. Thereby, the sensation of the stimulation as well as the effect of the treatment can be further improved if it is provided that at the end of the stimulation cycle sequence, the control circuit feeds a control signal to the amplifiers provided in the output channels, which said control signal continuously decreases from in each case one stimulation cycle to the next following stimulation cycle the intensity of the therapeutic current fed to a respectively considered stimulation electrode, the intensity being considered as average over the respective current flow time interval.

With regard to the energy supply of the device according to the invention, an embodiment is preferred which is characterized in that for supplying the amplifiers provided in the output channels, a voltage transformer with a bipolar output is provided which, for its part, is supplied by the battery provided in the device. In this manner, supplying the amplifiers can be carried out with a battery which is formed from only one cell or few cells and, in a given space, has a relatively high energy content which enables a stimulation operation over several days. Another extension of the treatment duration possible with the device can be achieved by minimizing the losses occurring in the mentioned voltage transformer. For this, a refinement of the aforementioned embodiment provides that in the connection supplying from the battery to the voltage transformer, a switching device is inserted which interrupts the supply during the current flow pauses present in the therapeutic current circuits as well as upon exceedance of a predefined limit value of the current drawn by the voltage transformer from the battery. Besides the energy-saving function, the switching device has the function of protection against overloading the battery and against exceeding predefined values of the therapeutic currents.

Another embodiment which is effective in terms of the best possible utilization of the energy contained in the supplying battery is characterized in that for supplying the micro-computer circuit, the digital-analog converter and potentially provided measurement signal circuits, a voltage transformer is provided which has an unipolar output and is connected to the battery, wherein said voltage transformer is bypassed with a Schottky diode and is activated only when the battery voltage falls, and delivers at its output a voltage that corresponds to the battery target voltage.

For setting the parameters of the therapeutic currents for the respective present treatment case, an embodiment of the device according to the invention is advantageous and preferred which is characterized in that the device has a wirelessly operating transmission device which is connected to the micro-computer circuit and serves, by means of an external control device, for entering parameters to be stored of the therapeutic currents provided for the respective treatment. Furthermore, it can advantageously be provided that the device has a wirelessly operating transmission device which is connected to the micro-computer circuit and serves for transmitting stored parameters of the therapeutic currents provided for the respective treatment to an external control and monitoring device.

As an external control device, a conventional computer can be used which has an interface to which an adaptor can be connected which is provided with a transceiver device.

For a wireless transmission, it is advantageously possible to use devices which operate in a band in the decimetric wave range provided for control purposes. However, other devices which transmit the control information in the infrared range can also be used. Also possible are simpler embodiments, wherein the control information, which corresponds to the parameters of the provided therapeutic currents, is stored in such a device during its fabrication.

BRIEF DESCRIPTION OF THE DRAWINGS

The invention is now further explained by means of examples with reference to the drawing in which exemplary embodiments are schematically illustrated. In the figures.

DETAILED DESCRIPTION OF VARIOUS AND PREFERRED EMBODIMENTS OF THE INVENTION

Figure 1:
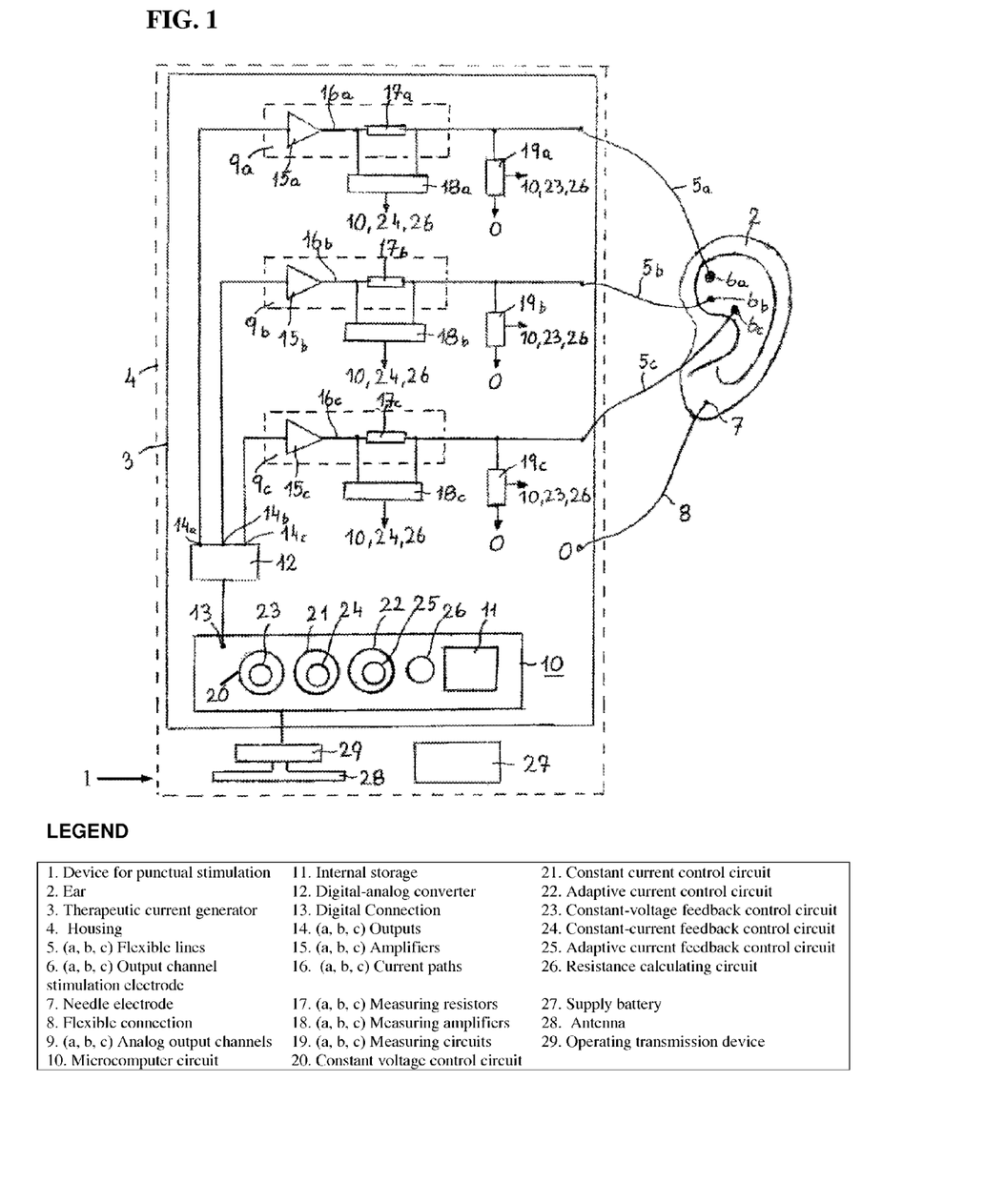
FIG. 1 shows an exemplary embodiment of a device configured according to the invention in a schematically illustrated block diagram.

The embodiment shown in FIG. 1 in a schematic block diagram of a device configured according to the invention is provided for the punctual stimulation of nerve endings which are located in the region of the ears and run to the brain stem nuclei.

This device 1 has a battery-powered therapeutic current generator 3 which arranged in a housing 4 which is to be worn in the region of an ear 2 at which the stimulation is to be performed. With regard to the dimensions of the device 1, it is to be mentioned that the illustration in FIG. 1 is intended to primarily illustrate the constructional and functional features, and the dimensions of the housing 4 enclosing the components of the device can usually be kept smaller than the dimensions of the ear 2. The battery-powered therapeutic current generator 3 contains a low-frequency therapeutic current-forming electronic circuit which feeds via flexible lines 5a, 5b, 5c the stimulation needle electrodes 6a, 6b, 6c to be arranged in the ear 2. A reference electrode which, in the illustrated case, is configured as a needle electrode 7 is connected via a flexible connection 8 to a reference potential point 0 of the device. The reference electrode 7 can also be configured in a different form, e.g. in the form of a surface electrode which, as illustrated, can be arranged at a flexible connection 8 or can also be attached in a mechanically different manner on the housing 4 of the device. Within the context of the mentioned electronic circuit, the current generator 3 has a plurality of analog output channels 9a, 9b, 9c, wherein each of these output channels is associated with its own stimulation electrode 6a, 6b, 6c and supplies the therapeutic current to these electrodes. The mentioned analog output channels are each individually connected on the input side to a micro-computer circuit 10 in which parameter values of the therapeutic currents provided for the respective treatment can be stored in a storage 11 to be available for a continuous readout. In the individual output channels 9a, 9b, 9c, in each case one amplifier 15a, 15b, 15c is provided which is controlled by a digital-analog converter 12 and is configured for bipolar output signals. Constructionally advantageous, the digital-analog converters are combined to form one unit, but can also be implemented separately. The digital-analog converter 12, for its part, is connected to a digital connection 13 of the micro-computer circuit 10. At least two of the mentioned output channels, which are each associated with their own stimulation electrode, preferably three such output channels, as illustrated, are provided. However, if desired, a greater number of such output channels and associated stimulation electrodes can be provided. As an amplifier 15a, 15b, 15c, preferably, an operational amplifier is provided.

In the current paths 16a, 16b, 16c located in the output channels 9a, 9b, 9c and running to the stimulation electrodes 6a, 6b, 6c, measuring resistors 17a, 17b, 17c are inserted which serve for measuring the intensity of the therapeutic currents. Connected to the individual measuring resistors 17a, 17b, 17c is in each case a measuring amplifier 18a, 18b, 18c, the output signal of which is a measure for the current strength of the therapeutic current, and this output signal is fed to the micro-computer circuit 10. Also provided at the output channels 9a, 9b, 9c are voltage measuring circuits 19a, 19b, 19c, each of them transmitting to the micro-computer circuit 10 a measurement signal which corresponds to the voltage which is present between the stimulation electrode 6a, 6b, 6c associated with the relevant output channel and the reference potential 0 or the reference electrode 7.

Provided in the micro-computer circuit 10 is a constant-voltage control circuit 20 which is optionally activatable by external actuation and which is operatively connected to the internal storage 11 for therapeutic current parameters and which, via the digital-analog converter 12, feeds a control signal via the outputs 14a, 14b, 14c of the digital-analog converter 12 to at least one amplifier 15a, 15b, 15c which are each provided in an output channel 9a, 9b, 9c, said control signal causing in the respective amplifier's 15a, 15b, 15c output circle connected to a stimulation electrode 6a, 6b, 6c the behavior of a constant-voltage source that is adjustable regarding the voltage value. It is preferably provided here, as illustrated in FIG. 1, that in the constant-voltage control circuit 20, a constant-voltage feedback control circuit 23 is integrated to which the measurement signal of the relevant voltage measuring circuit 19a, 19b, 19c is fed as an actual signal. Furthermore, a constant-current control circuit 21 is provided which is optionally activatable by external actuation and is likewise operatively connected to the internal storage 11 for therapeutic current parameters and which feeds a control signal via the digital-analog converter 12, at the outputs 14a, 14b, 14c of which the amplifiers 15a, 15b, 15c are connected, to at least one of these amplifiers, said control signal causing in this amplifier's 15a, 15b, 15c output circuit connected to a stimulation electrode 6a, 6b, 6c the behavior of a constant-current source that is adjustable with regard to the current strength; here, in the constant-current control circuit 21, a constant-current feedback control circuit 24 is integrated to which the output signal of the measuring amplifier 18a, 18b, 18c associated with the respectively considered amplifier 15a, 15b, 15c is fed as an actual signal.

Furthermore, provided in the micro-computer circuit 10 is an adaptive-current control circuit 22 which is optionally activatable by external actuation and operatively connected to the internal storage 11 for therapeutic current parameters and which feeds a control signal to at least one amplifier 15a, 15b, 15c provided in an output channel 9a, 9b, 9c, said control signal causing in the respective amplifier's 15a, 15b, 15c output circuit connected to a stimulation electrode 6a, 6b, 6c a current strength and stimulation voltage behavior which adapts to the resistance value in this output circuit and corresponds to the relations $I = k \cdot R$ and $U = k \cdot R^2$, wherein k is a selectable constant. Preferably, integrated in the adaptive-current control circuit 22 is an adaptive current feedback control circuit 25 to which a resistance measurement value obtained from the measurement signal of the respective voltage measuring circuit 19a, 19b, 19c and the output signal of the respective measuring amplifier 18a, 18b, 18c is fed as an actual signal. In order to form the resistance measurement value, a resistance calculating circuit 26 is provided in the micro-computer circuit 10.

The resistance determination or also a voltage measurement with an above-mentioned voltage measuring circuit can also be used for checking if the stimulation electrodes have been correctly arranged during the placement.

In the sense of a diverse usability of the device it is possible, as illustrated in FIG. 1, to provide the three different control circuits 20, 21, 22 in the micro-computer circuit 10; however, it is also possible in the sense of simplifying or in the sense of tailoring the device for certain therapy forms to provide only one or two of these control circuits. It is also possible, as illustrated, to provide in the housing 4 of the device, the supply battery 27 and the wirelessly operating transmission device 29 which, e.g., is equipped with an antenna 28 and serves for entering parameters to be stored of the therapeutic currents provided for the respective treatment and which, for its part, is connected to the micro-computer circuit 10.

It is constructionally and functionally advantageous if it is provided that the micro-computer circuit 10 with its storage 11 and the control circuits 20, 21, 22, 26, and preferably also the components which form the output channels 9a, 9b, 9c and are associated with these output channels, are integrated in a microchip. Components serving for a wireless transmission of parameters of therapeutic currents can also be involved in such an integration.

Figure 2:
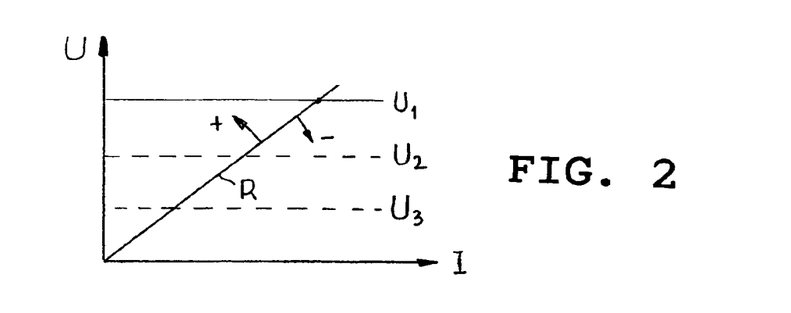
FIGS. 2, 3 and 4 show diagrams which illustrate different ways of controlling therapeutic currents provided for the stimulation.
Figure 3:
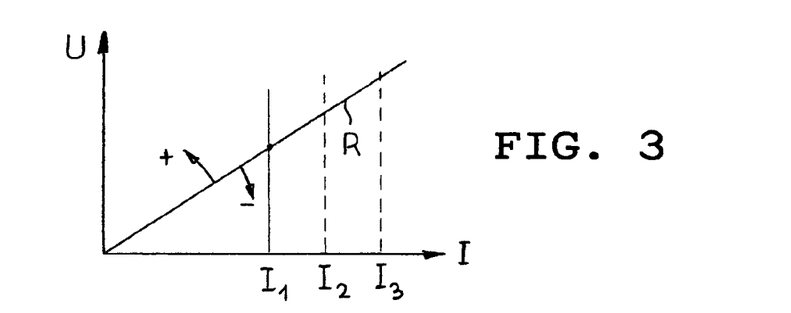
Figure 4:
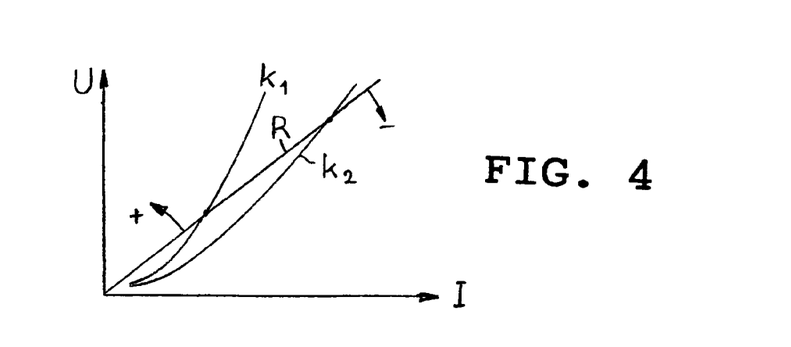

FIGS. 2, 3 and 4 illustrate the relationship between the values of current and voltage acting on the electrodes and of the electrical resistance which is present in different operating modes in the respective current circuit which runs from the amplifier located in the respective output channel through the associated stimulation electrode.

FIG. 2 shows in this connection when in the mentioned current circuit running through the stimulation electrode, the amplifier present in the respective output channel has the behavior of an adjustable constant-voltage source. A plurality of selectable voltage values are designated with U1, U2 and U3, and the current flowing in each case results from the intersection of the resistance line designated with R with the voltage value set in each case. The voltage (U1, U2, U3) set in each case is applied to the stimulation electrode and the current I flowing through the stimulation electrode decreases with increasing resistance in the circuit of the stimulation electrode and increases with decreasing resistance. An increase of the resistance R is indicated in FIG. 2 with +, and a decrease of the resistance R is indicated with −.

FIG. 3 illustrates the relationships when in the respective output circuit of an amplifier provided in an output channel, which said output circuit is connected to a stimulation electrode, the behavior of a constant-current source adjustable regarding the current strength is present. Three optionally adjustable current values I1, I2, I3 are indicated. The voltage occurring at the stimulation electrode considered in each case increases with increasing resistance and decreases with decreasing resistance.

FIG. 4 shows the relationships in the case of a current strength and stimulation voltage behavior, with the behavior adapting to the resistance value present in the current circuit of a stimulation electrode and an adaptive control of the amplifier corresponding to the relations $I=k \cdot R$ and $U=k \cdot R^2$ The values of the current strength of the current flowing through the relevant stimulation electrode and the values of the voltage applied to stimulation electrode, which values belong together in each case, lie on parable-like characteristic curves, and two such characteristic curves which apply to different values of k are drawn in FIG. 4 and are designated with k1 and k2. The values of current strength and stimulation voltage resulting from a certain value of the resistance in the current circuit flowing through the stimulation electrode are given in each case by the intersection of the resistance line R with the characteristic line that corresponds to the respective value k. When the resistance value decreases, the current and the voltage in the stimulation circuit decrease and, conversely, the current and the voltage in the stimulation circuit increase as the resistance acting in the stimulation circuit increases. Such an adaptive behavior of the values of current and voltage at the respectively considered stimulation electrode offers the advantage of an adaptation to the sensation existing in many patients, according to which in the case of low values of the stimulation current, changes of the latter are intensely felt whereas in the case of high values of the stimulation current, changes of the same are felt to a significantly lesser extent.

A stimulation treatment usually lasts over relatively long periods, wherein time intervals during which a current flow to the stimulation electrodes takes place alternate with time intervals in which the current flow is interrupted. In most cases, short current flow time intervals and short inactive time intervals are provided in an alternating sequence and after a relatively high number of such cycles, relatively long pauses are provided, e.g. with a duration of 1 hour.

Figure 5:
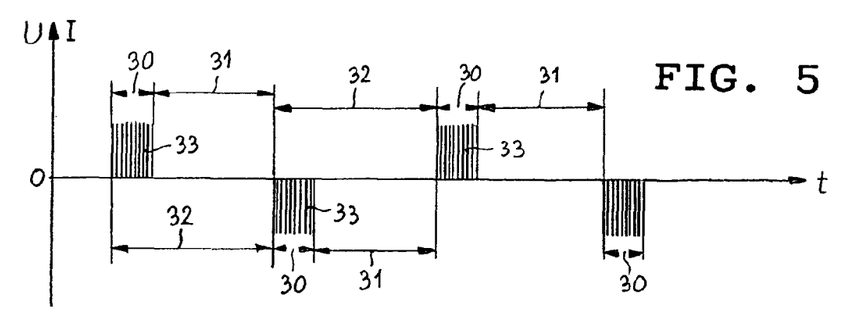
FIGS. 5 to 10 show time diagrams which show the curve of the currents provided for the stimulation, which occur in different embodiments of the device according to the invention.

FIG. 5 shows the chronological sequence of such a stimulation, wherein current flow time intervals 30 alternate in a cyclical succession with inactive time intervals 31 and in each case one current flow time interval 30 and one inactive time interval 31 together form one stimulation cycle 32. In the current flow time intervals 30, the therapeutic current has the form of a packet of successive pulses 33, each of which last, e.g., several milliseconds. During each current flow time interval 30, in the case illustrated in FIG. 4 at the beginning of said interval, a polarity reversal of the therapeutic current takes place.

Figure 6:
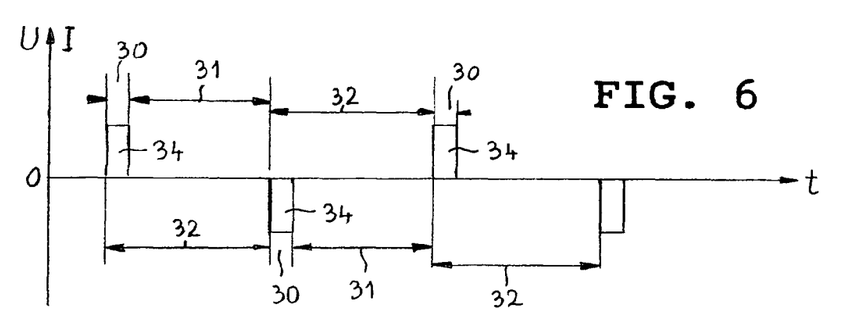

FIG. 6 shows a variant of the chronological sequence of a stimulation treatment illustrated in FIG. 5, wherein in the case illustrated in FIG. 6, the therapeutic current flowing in the current flow time intervals 30 has in each such time interval 30 the form of a single pulse 34. At the beginning of each current flow interval 30, analog to the sequence illustrated in FIG. 5, a polarity reversal of the therapeutic current takes place.

In the FIGS. 5 and 6, the stimulation pulses are illustrated with a constant voltage value, corresponding to the behavior as a constant-voltage source of the amplifiers provided in the output channels of the device according to the invention.

Figure 7:
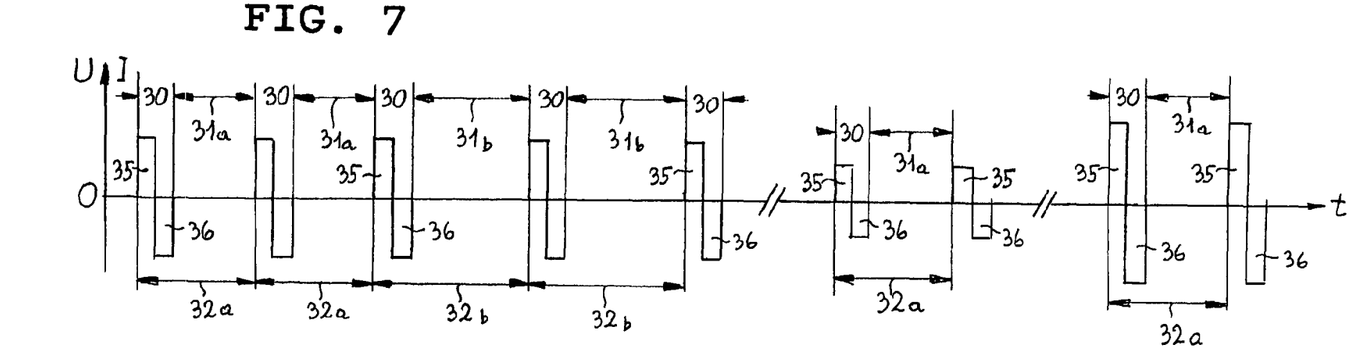

FIG. 7 shows the chronological sequence of a further form of the stimulation. Here, the therapeutic current flowing in the current flow time intervals 30 has the form of double pulses 35, 36, the polarities of which are opposing each other, wherein the polarity reversal takes place in the course of the current flow time intervals 30. In this embodiment, which focuses in particular on an adaptive feedback control of the therapeutic current, it is provided that the intensity of the therapeutic current is varied for adapting to the conditions present in each case. Here, on the one hand, the inactive time intervals of the stimulation cycles are varied whereby also the duration of the stimulation cycles changes, wherein, e.g., the inactive time intervals 31b are longer than the inactive time interval 31a and, correspondingly, the stimulation cycles 32b are longer than the stimulation cycle 32a. In this manner, a variation of the current strength's average determined over the duration of a stimulation cycle is obtained through the variation of the duration of the stimulation cycle. The current strength is to be considered here based on the sum of the individual pulses 35, 36 while disregarding the polarity reversal. Furthermore, in the sequence of a stimulation process illustrated in FIG. 7, a variation of the amplitude of the therapeutic currents is provided.

Figure 8:
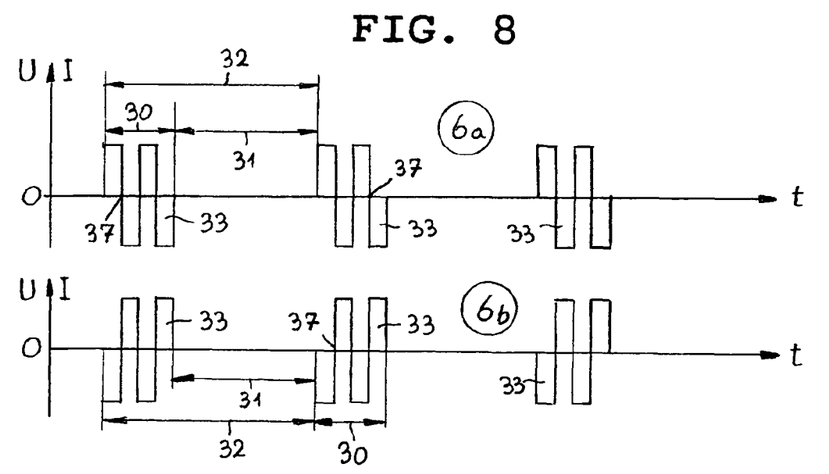

FIG. 8 shows in a chronological sequence the therapeutic currents which are present at two stimulation electrodes which are associated in each case with one output channel of the device according to the invention. Here, the therapeutic currents are formed in the current flow intervals 30 in each case by a packet of successive pulses 33, wherein in each case during the transition from one packet of these pulses 33 to the next packet of these pulses, a polarity reversal 37 takes place. With regard to a reference electrode connected to the therapeutic current circuits, the therapeutic current fed in the current flow intervals 30 to the stimulation electrode 6a has a different polarity with respect to the therapeutic current fed in the current flow time interval 30 to the stimulation electrode 6b. Since, furthermore, the intensities of the pulses 33 of the therapeutic current fed to the stimulation electrode 6a are equal to the intensities of the pulses 33 of the therapeutic current fed to the stimulation electrode 6b and compensate each other due to the different polarities in the respectively considered point in time, this results in that here no therapeutic current flows through a reference electrode that is connected to the therapeutic current circuits. In the case of unequal intensities of the pulses of the therapeutic current fed to the stimulation electrodes 6a, 6b, only a partial compensation is obtained and a current flow, although a reduced one, through such a reference electrode takes place.

Figure 9:
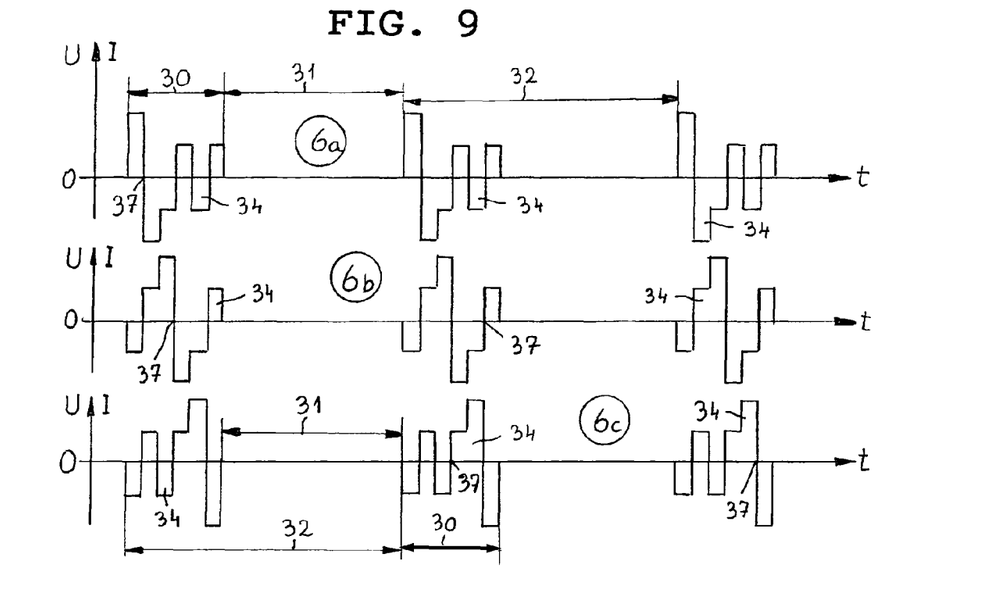

FIG. 9 shows the chronological sequence of therapeutic currents which are fed to three stimulation electrodes 6a, 6b, 6c, wherein these stimulation electrodes, for their parts, are associated in each case with one output channel of a device configured according to the invention. The therapeutic currents fed to the individual stimulation electrodes 6a, 6b, 6c are formed in each current flow time interval 30 by a single pulse 34, wherein in each of these single pulses, a plurality of chronologically successive intensity changes and polarity reversals 37 are provided. The intensity changes of the therapeutic currents take place incrementally. It applies here that the intensity changes taking place at a respectively considered stimulation electrode run counter to intensity changes taking place at one or a plurality of other respectively considered stimulation electrodes. Through mutual adaptation of the extent of the intensity changes it is achieved that at each considered point in time within the current flow time intervals, the therapeutic current fed to each individual stimulation electrode 6a, 6b, 6c is compensated with regard to intensity and polarity by the therapeutic currents fed to the in each case two other stimulation electrodes 6a, 6b, 6c. This results in that no therapeutic current flows through a reference electrode provided at the device. Also, potentially occurring contact uncertainties at one of the stimulation electrodes are largely compensated automatically, wherein also in such a case, a compensation current potentially flowing through a reference electrode remains low.

Figure 10:
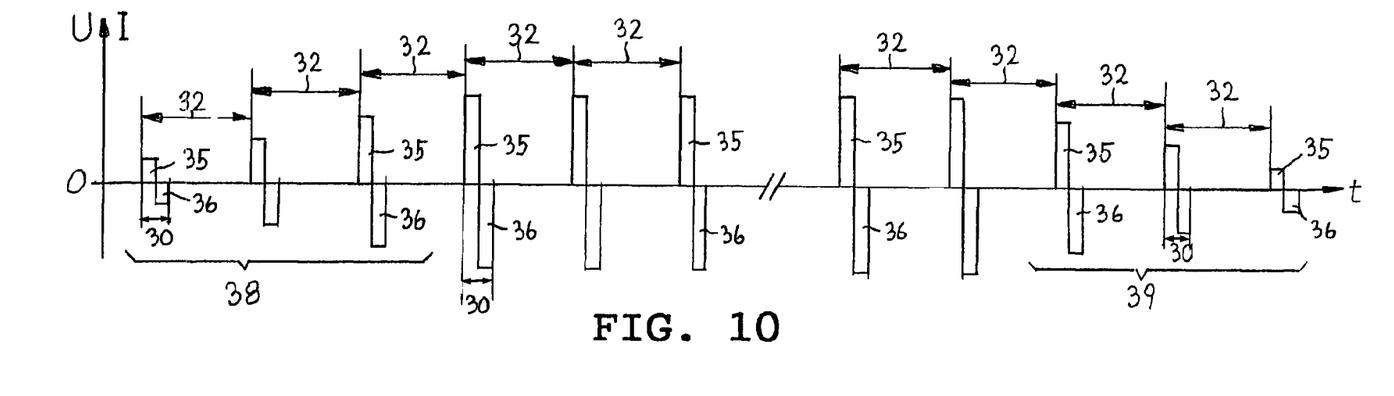

For the flow of the therapeutic current illustrated in FIG. 10, it is provided that at the beginning 38 of a stimulation cycle sequence formed by a multiplicity of successive stimulation cycles 32, during a plurality of successive stimulation cycles, the intensity of the therapeutic current fed to a respectively considered stimulation electrode 6a, 6b, 6c, the intensity being considered as average over the respective current flow time interval 30, is continuously increased from in each case one stimulation cycle 32 to the next following stimulation cycle, and is subsequently maintained during a multiplicity of successive stimulation cycles on the previously achieved level of intensity. At the end 39 of the stimulation cycle sequence, the intensity of the therapeutic current fed to a respectively considered stimulation electrode is continuously reduced from in each case one stimulation cycle to the next following stimulation cycle.

The features in the exemplary embodiments of the time sequences of therapeutic currents provided for the stimulation are not to be viewed only in connection with the respective exemplary embodiment but can also be combined with each other within the context of the invention. In particular, the time sequences as shown in the FIGS. 5, 6, 7 and 10, which, for a better understanding, are illustrated for one output channel, can also be used, according to the concept of the invention, for a plurality of output channels, wherein regarding the parameters of the stimulation pulses to be provided, in all cases different possibilities exist. It is therefore possible in the different exemplary embodiments to optionally provide packets of successive pulses or single pulses, wherein different variants of polarity reversals and intensity changes are feasible. Apart from the supply of different currents to the different stimulation electrodes as mentioned here, a concurrent supply to these electrodes is optionally also possible.

Figure 11:
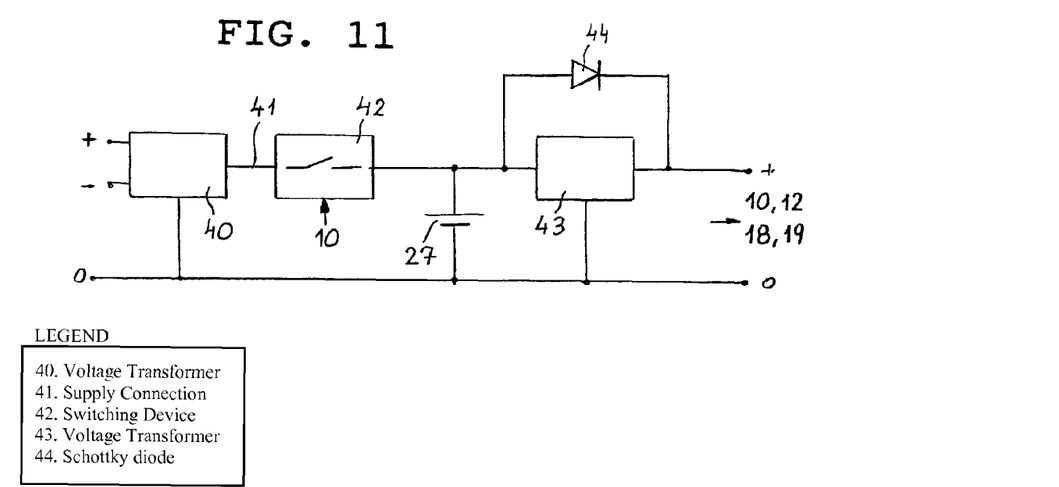
FIG. 11 shows a block diagram of an embodiment of a voltage supply circuit provided in the device according to the invention.

In the embodiment illustrated in FIG. 11 of an operating voltage supply circuit provided in a device configured according to the invention, a voltage transformer 40 with a bipolar output is provided for supplying the amplifiers 15a, 15b, 15c provided in the output channels 9a, 9b, 9c, wherein said voltage transformer, for its part, is supplied by the battery 27 provided in the device. In the supply connection 41 running from the battery 27 to the voltage transformer 40, a switching device 42 is inserted which, while being controlled by the micro-computer circuit 10, interrupts the supply to the voltage transformer 40 during the current flow pauses occurring in the therapeutic current circuits and also in the case of exceedance of a predefined limit value of the current drawn by the voltage transformer 40 from the battery 27. For supplying the micro-computer circuit 10, the digital-analog converter 12 and potentially provided measurement signal circuits 18 (18a, 18b, 18c), 19 (19a, 19b, 19c), a voltage transformer 43 is provided which has an unipolar output and is connected to the battery 27, wherein said transformer is bypassed with a Schottky diode 44 and is activated only when the battery voltage falls, and delivers at its output a voltage that corresponds to the battery target voltage.

The transmission device 29 is preferably set up for entering parameters to be stored of the therapeutic currents provided for the respective treatment as well as for transmitting to an external control and monitoring device the parameters of the therapeutic current provided for the respective treatment, which said parameters are stored in the storage 11 of the micro-computer circuit 10.

The invention claimed is:

1. A device for the punctual stimulation of endings of nerves which are located in the region of the ears and run to the brainstem nuclei, said device comprising:
 a housing adapted to be located in the region of the ear, and
 a battery-powered therapeutic current generator arranged in the housing comprising:
  at least one electronic therapeutic current circuit adapted to form a low-frequency therapeutic current,
  a digital-analog converter,
  a micro-computer circuit comprising:
   an input side,
   a digital connection,
   an internal storage configured to: (i) store parameter values of therapeutic currents provided for a respective treatment, and (ii) render the parameter values available for a continuous readout, and
   an adaptive-current control circuit which is operatively connected to the internal storage;
  a plurality of analog output channels each comprising at least one amplifier having a output circuit, wherein said amplifier is adapted to be controlled by said digital-analog converter and is configured for bipolar output signals, wherein the output channels are each individually connected to the input side of the micro-computer circuit and are adapted to control the therapeutic current;
 at least one stimulation needle electrode adapted to be positioned at a nerve ending and being associated with each of the output channels; and
 at least two flexible lines connecting the therapeutic current generator to each of said stimulation needle electrodes,
 wherein the adaptive-current control circuit, via the digital-analog converter, is adapted to:
  (i) feed a control signal to the at least one amplifier, and
  (ii) cause, via said control signal, in the output circuit of said amplifier, which is connected to one of the output channel stimulation needle electrodes, a current strength (I) and stimulation voltage behavior (U) which adapts to resistance value (R) in the output circuit and corresponds to relations
 $I = k \cdot R$ and $U = k \cdot R^2$,
 wherein k is a selectable constant.

2. The device of claim 1, wherein at least one the amplifier is an operational amplifier.

3. The device of claim 1, further comprising measuring resistors and measuring amplifiers, wherein in the output channels, the measuring resistors for current measurement are located in current paths running to the stimulation needle electrodes, and for each output channel one of the measuring amplifiers is connected to the individual measuring resistors, and wherein the measuring amplifiers are adapted to produce an output signal that is a measure for a strength of the therapeutic current and is fed to the micro-computer circuit.

4. The device of claim 1 further comprising a reference potential point and at least one voltage measuring circuit, wherein said at least one voltage measuring circuit is provided at least at one of the output channels, and wherein said at least one voltage measuring circuit is adapted to send a measurement signal to the micro-computer circuit, said measurement signal corresponding to a voltage which is present between (i) the stimulation needle electrode associated with the relevant output channel and (ii) the reference potential point which is located in the therapeutic current generator.

5. The device of claim 1, wherein the micro-computer circuit further comprises a constant-voltage control circuit which is operatively connected to the internal storage and which, via the digital-analog converter, is adapted to feed a further control signal to the at least one amplifier, wherein the amplifier's output channel, due to said further control signal, is adapted to behave as a constant-voltage source that is adjustable regarding a voltage value.

6. The device of claim 5, wherein the constant-voltage control circuit comprises a constant-voltage feedback control circuit and at least one voltage measuring circuit adapted to feed a measuring signal to the constant-voltage feedback control circuit.

7. The device according to claim 1, wherein the device further comprises at least one voltage measuring circuit and at least one measuring amplifier and wherein the adaptive-current control circuit further comprises an adaptive-current feedback control circuit adapted to be fed (i) a resistance measurement value obtained from a measurement signal of the voltage measuring circuit and (ii) an output signal of the measuring amplifier of a current measurement as an actual signal.

8. The device of claim 1, wherein the adaptive-current control circuit is adapted to form, (i) via said control signal, in a cyclical succession, time intervals in which a current flow to the stimulation electrodes takes place and time intervals in which the output channels are inactive, and (ii) via one current flow time interval and one inactive time interval together, one stimulation cycle causing a variation of the current strength's average determined over a duration of a stimulation cycle by varying the duration through the control signal.

9. The device of claim 1 further comprising a reference potential point, wherein the stimulation needle electrodes are adapted to have, during a current flow of the therapeutic currents fed to the stimulation needle electrodes of each output channel, in a respectively considered point in time, different polarities regarding the reference potential point that is connected with the at least one electronic therapeutic current circuit.

10. The device of claim 9 wherein the therapeutic currents fed to the stimulation needle electrodes of each output channel are adapted to compensate each other in the respectively considered point in time so that no therapeutic current flows through a reference electrode.

11. The device of claim 9, wherein the adaptive-current control circuit, via said control signal, is adapted to, in a cyclical succession form (i) time intervals in which a current flow to the stimulation needle electrodes takes place and (ii) time intervals in which the output channels are inactive, wherein one current flow time interval and one inactive time interval together form one stimulation cycle, and the adaptive-current control circuit, via the therapeutic current in form of a packet of successive pulses or in the form of a single pulse that flows in the current flow time intervals is adapted to cause a polarity reversal at each current flow time interval.

12. The device of claim 11, wherein the polarity reversal is caused in the course of the current flow time intervals.

13. The device of claim 1, wherein the adaptive-current control circuit is adapted to feed a control signal to the amplifiers so that said control signal, in a cyclical succession, forms time intervals in which a current flow to the stimulation needle electrodes takes place and time intervals in which the output channels are inactive, wherein one current flow time interval and one inactive time interval together form one stimulation cycle that causes in the course of the individual current flow time intervals one or a plurality of changes of the intensity of the therapeutic currents fed to the stimulation needle electrodes, wherein the intensity changes taking place at a respectively considered stimulation needle electrode run counter to the intensity changes taking place at one or a plurality of other respectively considered stimulation needle electrodes (n).

14. The device of claim 13, comprising three output channels with one of said stimulation needle electrodes in each of said three output channels resulting in three stimulation needle electrodes, and the therapeutic current, which is fed within the current flow time intervals to one of said three stimulation needle electrodes is compensated with regard to intensity and polarity at each respectively considered point in time by the therapeutic currents which are fed to the two other stimulation needle electrodes of the three stimulation needle electrodes.

15. The device of claim 13, wherein the therapeutic currents fed to the stimulation needle electrodes in each current flow time interval are formed by a single pulse and in each of these single pulses, a plurality of intensity changes and at least one polarity reversal are provided in chronological succession.

16. The device claim 13, wherein the one-time or repeated change of the therapeutic current intensity provided in the individual current flow intervals takes place incrementally.

17. The device of claim 1, wherein the micro-computer circuit is integrated in a microchip.

18. The device of claim 1 further comprising a battery and a voltage transformer with a bipolar output supplied by said battery and wherein the battery is adapted to supply the at least one amplifier.

19. The device of claim 18 further comprising a switching device and a supply connection running from the battery to the voltage transformer into which said switching device is inserted and which is adapted to interrupt a supply (i) during current flow pauses present in the therapeutic current circuits as well as (ii) when a predefined limit value of the current drawn by the voltage transformer from the battery is exceeded.

20. The device of claim 1 further comprising a voltage transformer which has an unipolar output and is connected to a battery, the voltage transformer being adapted to supply the micro-computer circuit, and the digital-analog converter and, wherein said voltage transformer is adapted to be bypassed with a Schottky diode and to be activated only when the battery voltage falls, and is also adapted to deliver at said unipolar output a voltage that corresponds to the battery target voltage.

21. The device of claim 1, wherein the device comprises a wirelessly operating transmission device which is connected to the micro-computer circuit and is adapted to allow, via an external control device, entry of parameters to be stored of the therapeutic currents provided for the respective treatment.

22. The device of claim 1 further comprising an external control and monitoring device, wherein the device comprises a wirelessly operating transmission device which is connected to the micro-computer circuit and is adapted to transmit stored parameters of the therapeutic currents provided for the respective treatment to the external control and monitoring device.

23. A method for the punctual stimulation of endings of nerves which are located in the region of the ears and run to the brainstem comprising:

providing the device of claim 1 further comprising a constant-voltage source which is operatively connected to the internal storage wherein the constant-voltage control circuit, via the digital-analog converter, feeds a further control signal to the at least one amplifier, wherein the amplifier's output channel is, as a result of said further control signal, adapted to behave as a constant-voltage source that is adjustable regarding a voltage value.

24. A device for the punctual stimulation of endings of nerves which are located in the region of the ears and run to the brainstem nuclei, said device comprising:

a housing adapted to be located in the region of the ear, and a battery-powered therapeutic current generator arranged in the housing comprising:

an electronic circuit adapted to form a low-frequency therapeutic current, a digital-analog converter, a micro-computer circuit comprising:

an input side, a digital connection, an internal storage configured to: (i) store parameter values of therapeutic currents provided for a respective treatment, and (ii) render the parameter values available for a continuous readout, and an adaptive-current control circuit which is operatively connected to the internal storage;

a plurality of analog output channels each comprising at least one amplifier which is controlled by said digital-analog converter and is configured for bipolar output signals, wherein the output channels are each individually connected on an input side to the micro-computer circuit and are adapted to control the therapeutic current;

at least one stimulation needle electrode adapted to be positioned at a nerve ending and being associated with each of the output channels; and at least two flexible lines connecting the therapeutic current generator to each of said stimulation needle electrodes, wherein the adaptive current control circuit is adapted to feed a control signal to the at least one amplifier, wherein the adaptive current control circuit, via said control signal, is adapted to, in a cyclical succession, form time intervals in which a current flow to the stimulation electrodes takes place and time intervals in which the output channels are inactive, wherein one current flow time interval and one inactive time interval together form one stimulation cycle at the beginning of a stimulation cycle sequence formed by a multiplicity of successive stimulation cycles, during a plurality of successive stimulation cycles from one stimulation cycle of said sequence to a next following stimulation cycle an intensity of the therapeutic current fed to a respectively stimulation needle electrode continuously increases, the intensity being considered as average over the respective current flow time interval, and subsequently maintains during a multiplicity of successive stimulation cycles within their current flow time intervals the previously achieved level of intensity of the therapeutic currents, wherein at an end of the stimulation cycle sequence, the control circuit feeds a control signal to the amplifiers provided in the output channels, with said control signal continuously decreasing, from the one stimulation cycle to the next following stimulation cycle, the intensity of the therapeutic current fed to a respectively stimulation electrode, the intensity being considered as average over the respective current flow time interval.

* * * * *